United States Patent [19]
Avila, Jr.

[11] Patent Number: 5,943,703
[45] Date of Patent: Aug. 31, 1999

[54] DETACHABLE EAR-PROTECTOR FOR USE WITH EYEGLASSES AND SUNGLASSES

[76] Inventor: Hector M. Avila, Jr., 234 E. Empire St., San Jose, Calif. 95112

[21] Appl. No.: 09/157,673

[22] Filed: Sep. 21, 1998

[51] Int. Cl.⁶ ........................................................ A61F 11/06
[52] U.S. Cl. .................................. 2/209; 2/13; 351/122; 351/123
[58] Field of Search ................................ 2/209, 13, 15; 24/3.3; 351/122, 123

[56] References Cited

U.S. PATENT DOCUMENTS

| | | | |
|---|---|---|---|
| D. 207,187 | 3/1967 | Gould | D57/1 |
| D. 212,393 | 10/1968 | Maiese | D57/1 |
| D. 371,150 | 6/1996 | Bolash, IV | D16/339 |
| 4,670,911 | 6/1987 | Dunford | 2/209 |
| 4,682,374 | 7/1987 | Geiser | 2/209 |
| 4,751,746 | 6/1988 | Rustin | 2/13 |
| 4,796,307 | 1/1989 | Vantine | 2/209 |
| 5,092,667 | 3/1992 | Bagley | 351/156 |
| 5,402,189 | 3/1995 | Gill | 351/44 |
| 5,421,037 | 6/1995 | Schulze | 2/452 |
| 5,718,002 | 2/1998 | Pavlak | 2/423 |

Primary Examiner—Diana L. Oleksa
Attorney, Agent, or Firm—Milton S. Gerstein

[57] ABSTRACT

An ear-protector is provided as a flexible element preferably made of PVC, having a first enlarged section used for covering over an ear, and a second, forwardly-extending, reduced mounting section extending from the first enlarged section. Each section has formed therein a vertical slit, forming together a pair of forwardly-positioned slits through which may be passed the temple part of eyeglasses or sunglasses, by which the ear-protector is mounted over an ear. The temple part of the eyeglasses is inserted through the pair of slits, so that the section of the temple part of the eyeglasses between the pair of slits is located exteriorly of the ear-protector, and whereby the second reduced section of the ear-protector and part of the first enlarged section of the ear-protector adjacent to the first section is bowed inwardly in a concave manner for forcing the ear-protector against the ear, whereby the ear-protector is snuggly positioned against the ear, for protecting the ear against cold and wind.

12 Claims, 3 Drawing Sheets

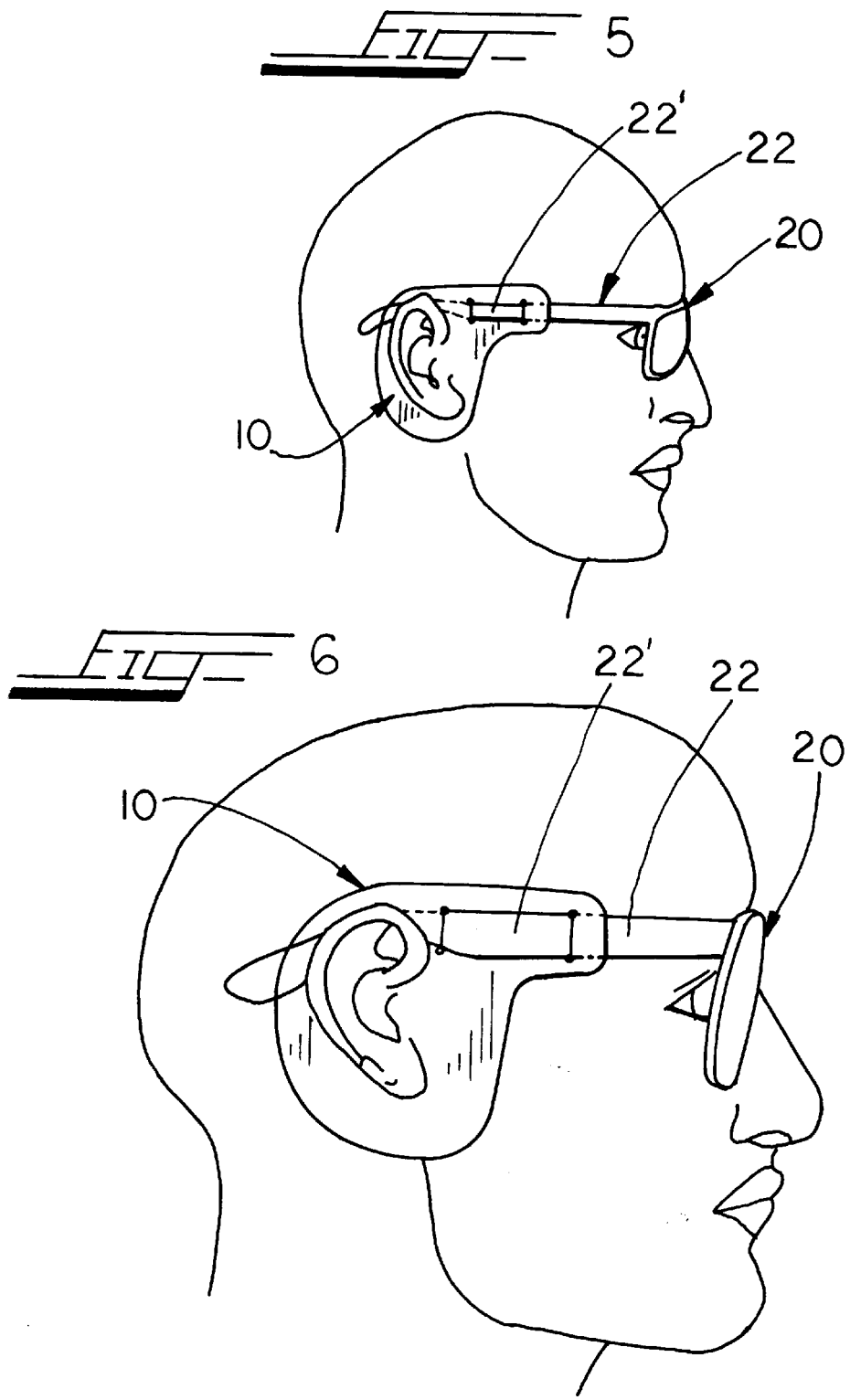

DETACHABLE EAR-PROTECTOR FOR USE WITH EYEGLASSES AND SUNGLASSES

BACKGROUND OF THE INVENTION

The present invention is directed to ear-protectors for protecting the ears from cold and wind, and has especial use for bicyclists and runners.

There are many prior art protectors for the ears, which protectors are mounted over the ears by means of the temples of eyeglasses or sunglasses worn by the person. For example, in U.S. Pat. No. 4,751,746, there is disclosed an ear-protector which is inserted the temple of sunglasses or eyeglasses. In this patent, the ear-protectors are made of cloth formed into a pocket which receives therein the ear being protected.

In U.S. Pat. No. 5,718,002, there are also disclosed ear-protectors that are formed as an integral part of protective eyeglasses. The ear-protectors are fixedly secured to the temples of the glasses.

In U.S. Pat. No. 4,670,911, there are disclosed detachable ear-coverings for use with goggles, and the like.

In U.S. Pat. No. 5,402,189, there is disclosed a side shield for use with eyeglasses, in order to protect the eyes from peripheral light and wind. The side shield contains a vertical slide-through for mounting the side shield to the temple of eyeglasses.

In all of these prior art patents that disclose wind protectors for ears, they suffer from the disadvantages that they are difficult to use, not detachable from the eyeglasses, and/or cannot be readily used with conventional eyeglasses or sunglasses.

Regarding U.S. Pat. No. 4,670,911, the shield thereof is for blocking for peripheral light to the eyes, and not for protecting the ears. Moreover, the shield of this patent is mounted to the interior of the temple of the eyeglasses, and, therefore, could not be used for covering the ear, since locating the shield along the rear portion of the temple of the glasses would prevent the ear-bows from engaging with the ear for holding the eyeglasses and the shield on the person. Moreover, the shield of this patent is not bowed or curved in use.

SUMMARY OF THE INVENTION

It is, therefore, the primary objective of the present invention to provide a shield or protector for protecting the ear of a person, which shield or protector is detachably secured to the temple of eyeglasses or sunglasses, which shield protects the ear from wind and cold.

It is, also, another objective of the present invention to provide a shield or protector for the ear of a person that has a pair of slits through which the temple of eyeglasses is inserted, the ear-protector being made of flexible material, so that, when the temple of the eyeglasses in inserted through the pair of slits, a forward-section of the shield is bowed inwardly to form a curve or bulge by which the ear-protector is urged against the ear in order to better protect the ear from wind and cold.

It is, also, another objective of the present invention to provide an ear-shield or ear-protector in which the temple of the eyeglasses or sunglasses is inserted through the pair of slits such, that the section of the temple of the eyeglasses or sunglasses between the two vertical slits is located exteriorly of the inwardly-curved, bowed forward-section, while the remaining section of the ear-bow section of the temple of the eyeglasses or sunglasses located rearwardly of the slits is positioned interiorly of the rear section of the ear-protector that is located rearwardly of the rear slit, in order that the ear-protector not interfere with the securement of the ear-bow portion of the temple of the glasses to the ear of the person.

According to the ear-protector of the present invention, there is provided a flexible element preferably made of PVC, having a first enlarged section used for covering over an ear, and a second, forwardly-extending, reduced mounting section extending from the first enlarged section. Each section has formed therein a vertical slit, forming together a pair of forwardly-positioned slits through which may be passed the temple part of eyeglasses or sunglasses, by which the shield is mounted over an ear. The temple part of the eyeglasses or sunglasses is inserted through the pair of slits, so that the section of the temple part of the eyeglasses or sunglasses between the pair of slits is located exteriorly of the shield, whereby the second reduced section of the ear-protector and part of the first enlarged section of the ear-protector adjacent to the first section is bowed inwardly in a concave manner for forcing the ear-protector against the ear, whereby the ear-protector is snugly positioned against the ear, for protecting the ear against cold and wind, whereby the ear is kept warm, and whereby the person may better hear his surroundings owing to the fact that the wind will no longer interfere with his hearing his surroundings. The rear portion of the ear-protector located rearwardly of the rear slit is positioned exteriorly of the ear-bow in order not to interfere with the securement of the ear-bow section of the temple to the ear of the person, and slopes outwardly in order to deflect the wind away from the ear.

BRIEF DESCRIPTION OF THE DRAWING

The invention will be more readily understood with reference to be accompanying drawings, wherein:

FIG. 5 is a side view showing the combination ear-protectors and eyeglasses on-the-person for protecting the ears from wind and cold; and FIG. 6 is an enlarged side view showing the combination ear-protectors and eyeglasses on-the-person for protecting the ears from wind and cold.

DETAILED DESCRIPTION OF THE INVENTION

Figure 1:
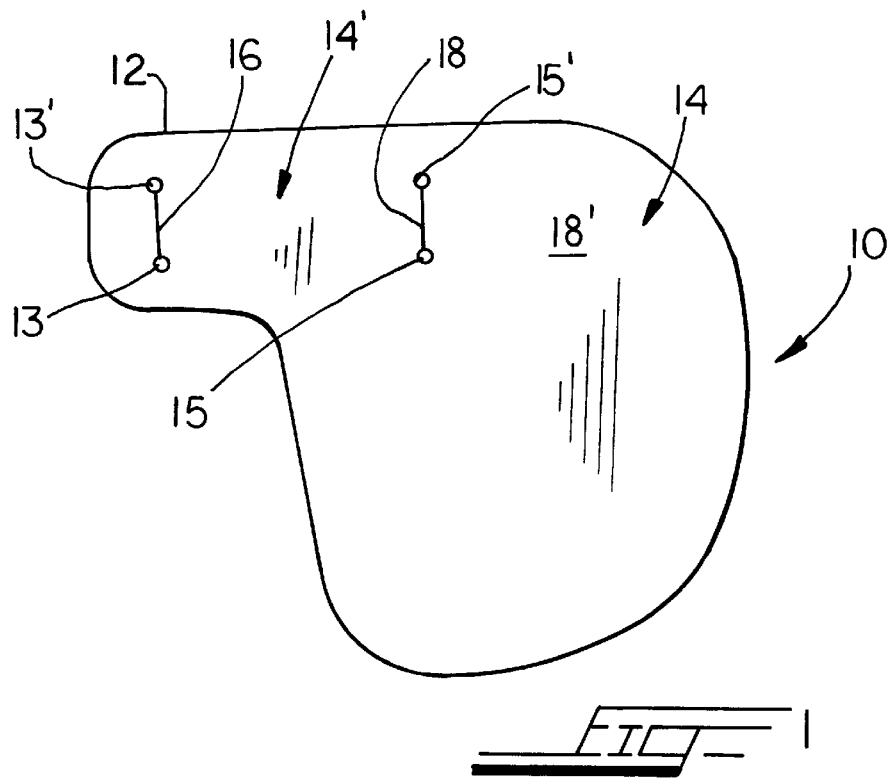
FIG. 1 is a plan view of the ear-protector of the present invention oriented for use for protecting the left ear.
Figures 2, 3:
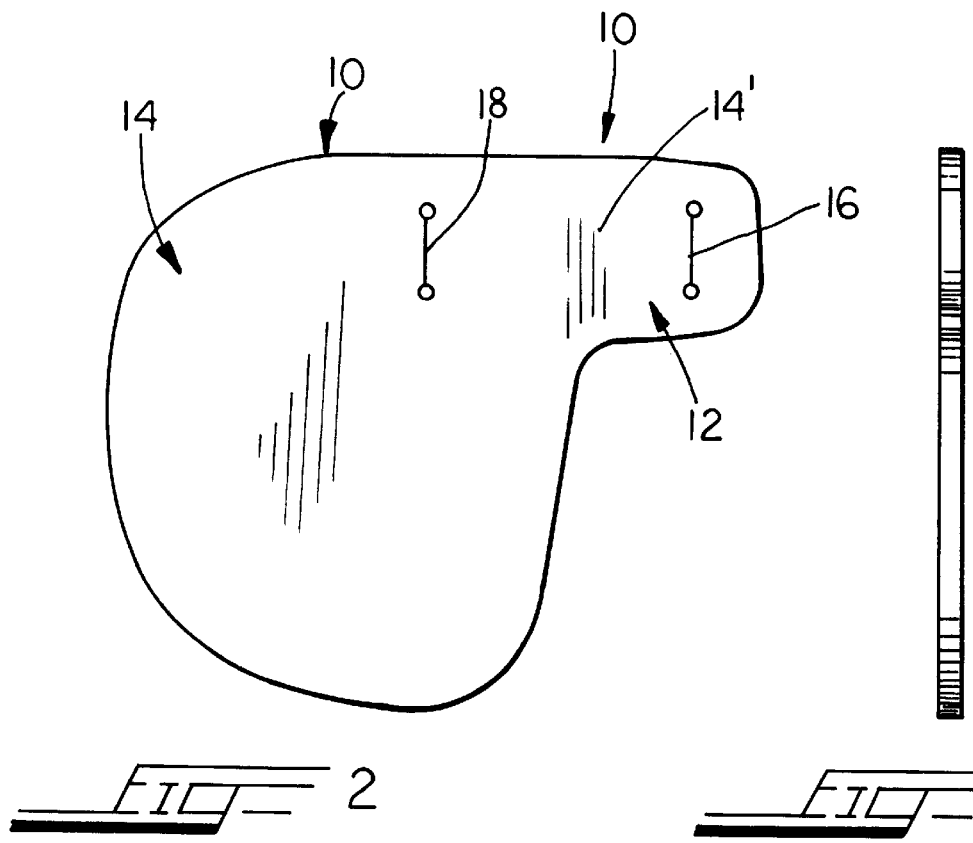
FIG. 2 is a plan view of the ear-protector of the present invention oriented for use for protecting the right ear.
FIG. 3 is a side view thereof.

Referring out to the drawings in greater detail, there is shown the ear-protector 10 of present invention. In FIG. 1, the ear-protector shown is oriented for use for covering or protecting the left ear of a person. In FIG. 2, there is shown the ear-protector in its orientation for protecting the right ear of a person. Whether the ear-protector 10 is use for the right ear or the left ear, the protector 10 is identical; only its orientation is reversed, depending upon which ear is being used. The ear-protector 10 is preferably made of PVC material, and in the preferred embodiment, is clear or translucent, having a thickness of approximately 0.080 mils.

As can be seen in FIGS. 1 and 2, the ear-protector 10 has a reduced forward-section 12 and an enlarged section 14. The enlarged section 14 is basically oblong or elliptical in shape, while the reduced forward-section 12 projects from the upper, forward part of the enlarged section, whereby the ear-protector 10 assumes a comma-like shape. The ear-protector 10 is provided with a pair of spaced-apart, vertical expanding slits or slots 16, 18. The slit 16 is formed in the reduced forward-section 12, while the other slit 18 is formed in the enlarged section 14. The forward section 12 is reduced in width in order to allow for the easier bending thereof. As explained hereinbelow, these slits 16, 18, are used for mounting the ear-protector 10 to the temple 22 of eyeglasses or sunglasses 20, as best seen in FIG. 4.

Each ear-protector 10 is mounted to a temple section 22, such that the section 14', located between the slits 16,18, faces interiorly, while the portion 22' of the temple 22 extending between the pair of slits 16,18 is positioned, or faces, exteriorly. As can also be seen In FIG. 4, the rear section 18' of each ear-protector 10, extending rearwardly of the rear slit 18, faces exteriorly, while the ear-bow section 22" of each temple section 22 faces interiorly. This is essential in order that the rear section 18' does not interfere with the securement of the ear-bow section 22" about the ear of the person. It is also important to the present invention that, because of the inward bowing or curving of the forward section 14', the forward section 14' produces a biasing force in the rear section 18' toward the ear of the person for which the protector 10 is designed to shield; that is, because the forward section 14' is bent, and because it has a reduced width, such a configuration produces a greater return-bias in the rear section 18', whereby the ear-protector 10 is more snugly and firmly juxtapositioned against the ear. Thus, the slits 16,18, perform a dual function: They allow insertion of the section 22' of the temple therethrough for positioning the ear-bow 22" exteriorly for mounting the ear-protector 10 to the eyeglasses thereby, and, secondly, because of the inward bowing of the forward section 14', biases the rear section 18' toward the ear for firm engagement thereagainst.

In the preferred embodiment, the ear-protector has a length, as taken in the direction along the length of the temple section of the eyeglasses, of 3¾ inches, and a width of 3¼. Each slit 16, 18 is about one inch in vertical length, and are approximately two inches apart, which provides the optimal bend or curvature to the forward section 14'. In order to aid in the expansion of each vertical slot 16, 18, there are provided end-holes or end-openings 13, 13' and 15, 15' for the slits 16, 18, respectively.

Figure 4:
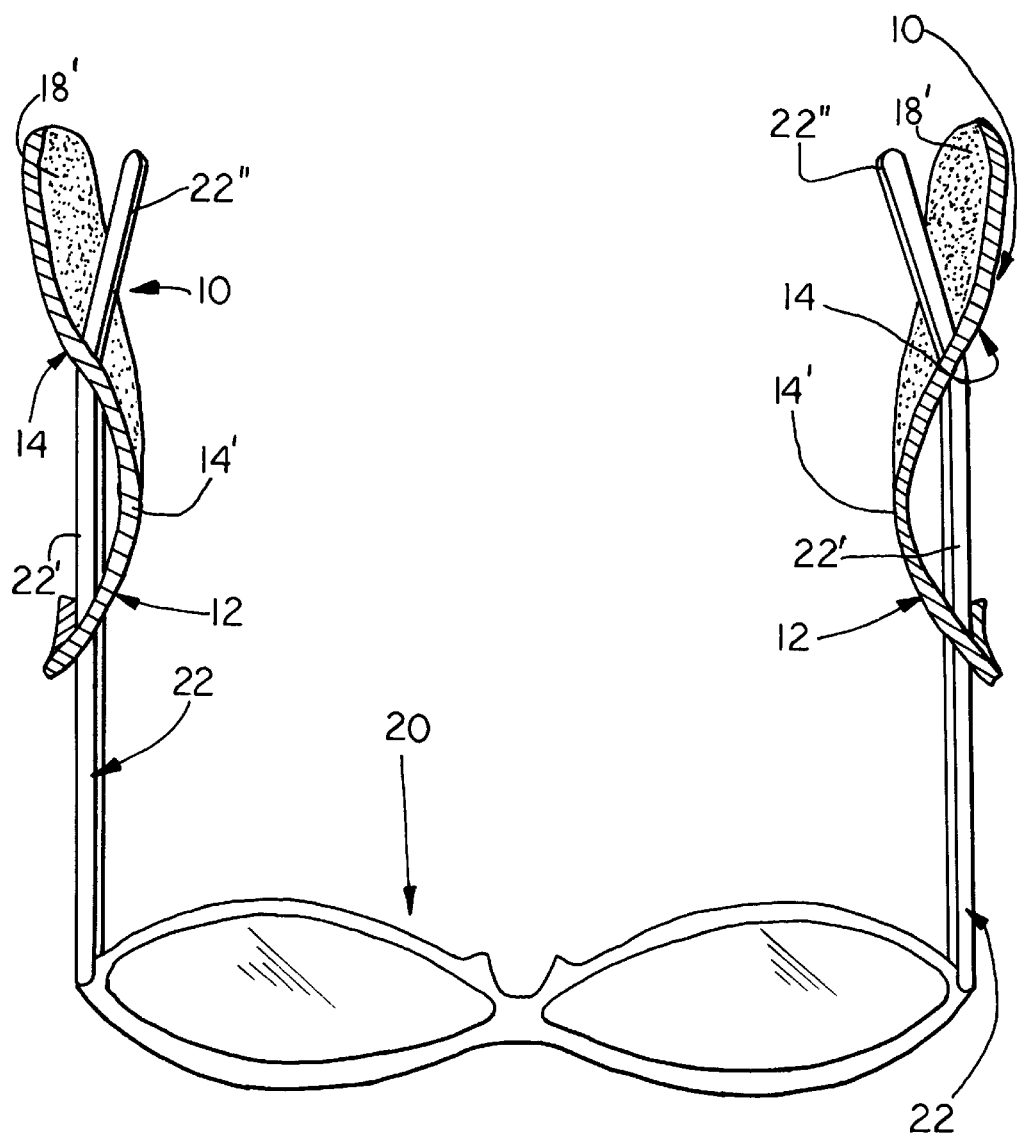
FIG. 4 is a top view showing the pair of ear-protectors detachably mounted to the temple sections of the eyeglasses.

As can be seen in FIG. 4, the rearward section 18' that covers the ear of the wearer is aerodynamically efficient by directing the wind flowing therepast away from the ear proper, whereby, besides protecting the ear from the cold, it is also deflects the wind away from the ear, not only preventing the wind from causing discomfort to the ear, but also eliminating the sound of the wind from the ear, thereby allowing the wearer to better hear his surroundings, whether he be running, jogging, cycling, and the like. As can be seen in FIG. 4, this rearward section 18' slopes slightly outwardly away from the ear to deflect the wind away from the ear. Thus, the inwardly-bowed section 14' not only biases the rearward section toward the ear, but also causes it to slope slightly away from the ear for wind-deflection, in order to allow the wearer to better hear his surroundings.

While a specific embodiment of the invention has been shown and described, it is to be understood that numerous changes and modifications may be made therein without departing from the scope and spirit of the invention as set forth in the appended claims. For example, a differently shaped ear-protector 10 is possible, as well as different materials, as long as the ear-protector is flexible.

What I claim is:

1. The combination of a pair of glasses worn over the eyes, and at least one ear-protector, said eyeglasses comprising a pair of temple sections, each temple section having an intermediate portion, and an end-portion for positioning adjacent an ear of a person wearing the eyeglasses, said at least one ear-protector comprising:

a flexible, main body portion having at least one portion thereof that covers over an ear of a person wearing said pair of glasses; said main body portion having an interior surface facing toward the ear being protected, and an exterior surface facing away therefrom;

said main body portion having a pair of spaced-apart, vertical slits cut therethrough, said pair of slits comprising a first, more-forward slit and a second, more-rearward slit, said main body portion having a forward section defined between said pair of slits, and a rearward section defined rearwardly of said more-rearward slit;

at least one of said pair of temple sections being inserted through said pair of slits with said intermediate portion thereof extending between said pair of vertical slits and exteriorly of said exterior surface of said forward section of said main body portion;

said end-portion of said temple section extending rearwardly from said more-rearward slit and interiorly of said interior surface of said at least one portion of said main body portion that covers over the ear; said end-portion being substantially coextensive with at least a portion of said rearward section of said main body portion;

said forward section of said main body portion being bowed inwardly toward the face of the wearer.

2. The combination of a pair of glasses, and at least one ear-protector, according to claim 1, wherein said end-portion of said at least one temple section of said pair of glasses, comprises an ear-bow for securing the pair of glasses, to the ear of the wearer.

3. The combination of a pair of glasses, and at least one ear-protector, according to claim 1, comprising a pair of ear-protectors, one said ear-protector for each said temple section.

4. The combination of a pair of eyeglasses, and at least one ear-protector, according to claim 1, wherein said ear-protector is made of PVC having a thickness of 0.080 mils.

5. The combination of a pair of glasses, and at least one ear-protector, according to claim 1, wherein said main body portion comprises a first, reduced-width portion, and a second, enlarged-width portion, said first, vertical slit being formed in said first, reduced-width portion.

6. The combination of a pair of glasses, and at least one ear-protector, according to claim 5, wherein said second vertical slit is formed in said second, enlarged-width portion of said main body portion.

7. The combination of a pair of glasses, and at least one ear-protector, according to claim 5, wherein said first, reduced-width portion and said second, enlarged-width portion together form a comma-shaped main body portion.

8. The combination of a pair of glasses, and at least one ear-protector, according to claim 5, wherein said forward section of said main body portion between said pair of slits is located partially in said first, reduced-width portion, and partially in said second, enlarged-width portion.

9. The combination of a pair of glasses, and at least one ear-protector, according to claim 1, wherein said rearward section of said main body portion slopes outwardly in the exterior direction away from a wearer's ear, in order to deflect wind, said slope of said rearward section being brought about by said inwardly-bowed forward section.

10. The combination of a pair of glasses, and at least one ear-protector, according to claim 1, wherein each of said slits comprises an upper and lower enlarged end-opening to aid in the insertion of one of said temple sections therethrough.

11. An ear-protector for protecting an ear from cold and wind in combination with a pair of glasses for wearing over a wearer's eyes, said ear-protector being capable of detachable mounting to said pair of glasses; said ear-protector comprising:

a flexible, main body portion having at least one portion thereof adapted to cover over an ear of a person; said main body portion having an interior surface adapted to face toward a wearer's ear being protected, and an exterior surface adapted to face away therefrom;

said main body portion having a pair of spaced-apart, vertical slits cut therethrough, said pair of slits comprising a first, more-forward slit and a second, more-rearward slit, said main body portion having a forward section defined between said pair of slits, and a rearward section defined rearwardly of said more-rearward slit;

said main body portion comprising a first, reduced-width portion, and a second, enlarged-width portion, said first, vertical slit being formed in said first, reduced-width portion, and said second vertical slit being formed in said second, enlarged-width portion of said main body portion;

said forward section of said main body portion between said pair of slits being located partially in said first, reduced-width portion, and partially in said second, enlarged-width portion;

said pair of glasses comprising a pair of temple sections, each temple section having an intermediate portion, and an end-portion for positioning adjacent an ear of a person wearing the glasses, one of said pair of temple sections being inserted through said pair of slits with the intermediate portion thereof extending between said pair of vertical slits and exteriorly of said exterior surface of said forward section of said main body portion, and whereby the end-portion of the temple section extends rearwardly from said more-rearward slit and interiorly of said interior surface of said at least one portion of said main body portion that covers over the ear; said forward section of said ear-protector being bowed inwardly, said rearward section of said main body portion being biased toward the ear being protected and sloped slightly outwardly in order to deflect wind.

12. A method of protecting an ear of a person using the combination of eyeglasses and an ear-protector, comprising the steps of (a) providing eyeglasses which comprise a pair of temple sections, each temple section having an intermediate portion, and an end-portion for positioning adjacent an ear of a person wearing the eyeglasses; (b) providing the ear-protector comprising a flexible main body portion having at least one portion thereof that covers over an ear of a person wearing the eyeglasses, the main body portion having an interior surface facing toward the ear being protected, and an exterior surface facing away therefrom; the main body portion having a pair of spaced-apart, vertical slits cut therethrough, the pair of slits comprising a first, more-forward slit and a second, more-rearward slit, the main body portion having a forward section defined between the pair of slits, and a rearward section defined rearwardly of the more-rearward slit;

(c) inserting a temple section through the pair of slits until the intermediate portion thereof extends between the pair of vertical slits and faces exteriorly of the exterior surface of the forward section of the main body portion;

(d) positioning the end-portion of the temple section rearwardly of the more-rearward slit and facing interiorly of the interior surface of the main body portion that covers over the ear;

(e) causing the forward section of the main body portion to be bowed inwardly toward the face of the wearer, and causing the rearward-section of the main body portion to be biased toward the ear and to slope slightly away from the ear, whereby the ear-portion is not obstructed for positioning at the ear.

\* \* \* \* \*